United States Patent [19]

Narciso et al.

[11] Patent Number: 5,454,794
[45] Date of Patent: Oct. 3, 1995

[54] STEERABLE LIGHT DIFFUSING CATHETER

[75] Inventors: Hugh L. Narciso, Jr.; Steven C. Anderson, both of Santa Barbara, Calif.

[73] Assignee: PDT Systems, Inc., Santa Barbara, Calif.

[21] Appl. No.: 138,134

[22] Filed: Oct. 15, 1993

[51] Int. Cl.⁶ ............................................. A61B 17/36
[52] U.S. Cl. ............................................. 604/280
[58] Field of Search .................... 604/95, 280, 101; 606/7, 96, 2, 3, 10–16, 191–194

[56] References Cited

U.S. PATENT DOCUMENTS

| | | | |
|---|---|---|---|
| 3,521,620 | 7/1970 | Cook | 604/95 |
| 4,753,223 | 6/1988 | Bremer | 604/95 |
| 4,765,330 | 8/1988 | Bach | 606/7 |
| 4,875,897 | 10/1989 | Lee | 606/7 |
| 4,920,980 | 5/1990 | Jackowski | 604/95 |
| 4,976,688 | 12/1990 | Rosenblum | 604/95 |
| 5,026,367 | 6/1991 | LeeKrone et al. | 606/7 |
| 5,078,684 | 1/1992 | Yasuda | 604/95 |
| 5,196,005 | 3/1993 | Doiron et al. | 606/7 |
| 5,207,669 | 5/1993 | Baker et al. | 606/7 |
| 5,231,989 | 8/1993 | Middleman et al. | 604/95 |
| 5,238,005 | 8/1993 | Imran | 604/95 |
| 5,257,991 | 11/1993 | Fletcher et al. | 606/7 |
| 5,269,777 | 12/1993 | Doiron et al. | 606/7 |
| 5,304,171 | 4/1994 | Gregory et al. | 606/7 |

*Primary Examiner*—C. Fred Rosenbaum
*Assistant Examiner*—Manuel Mendez
*Attorney, Agent, or Firm*—Michael G. Petit

[57] ABSTRACT

A steerable catheter is disclosed which can treat luminal surfaces such as those occurring in the vascular tree, pulmonary tree, gastrointestinal tract, urological organs, etc. with Photodynamic Therapy (PDT) or other optical diffusing treatments. The catheter, which may include an inflatable balloon portion, has a light diffusing tip which can be deflected allowing the catheter to be steered precisely. The light diffusing tip on the steerable catheter is able to gain access to and enter virtually any sub-branch of the luminal system being treated. Since this catheter does not require a guidewire lumen for insertion, the profile is reduced. A low profile device allows treatment light to be delivered to the walls of the most distal, small diameter lumen.

3 Claims, 6 Drawing Sheets

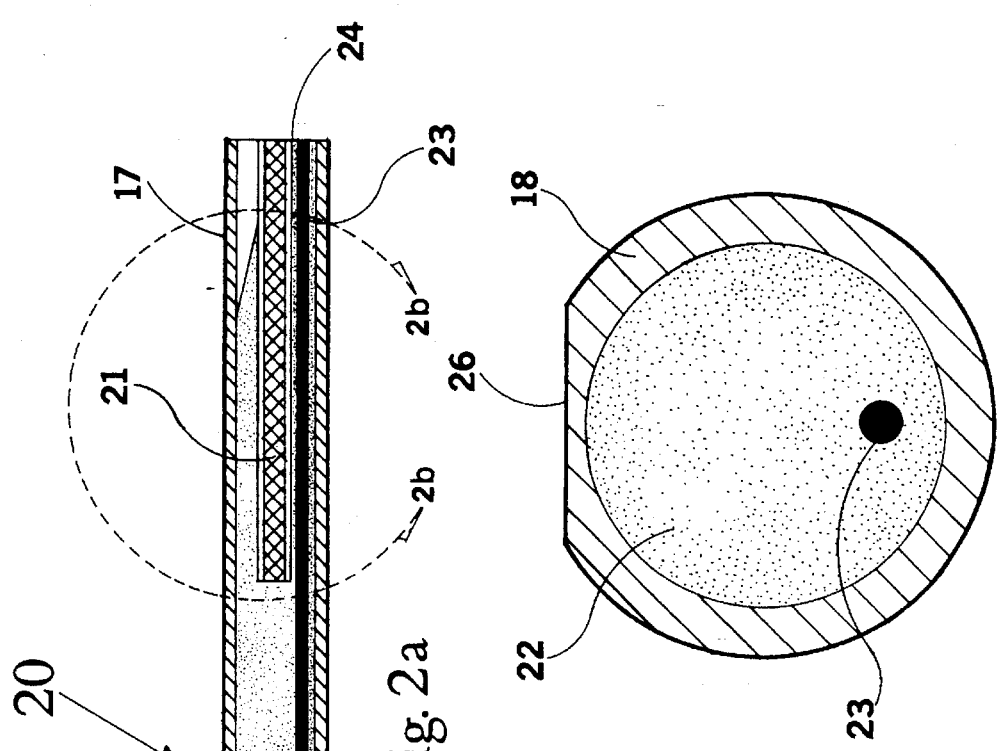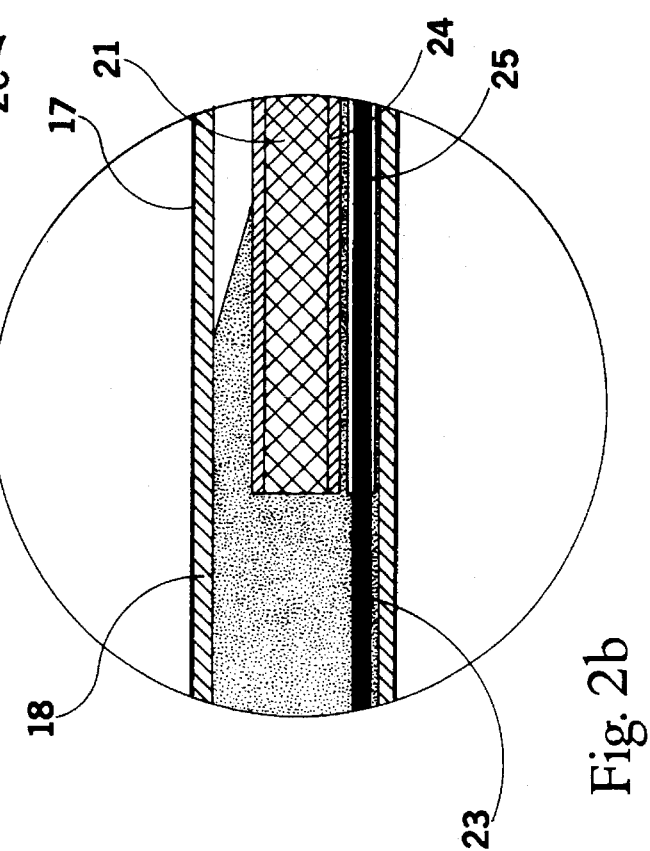

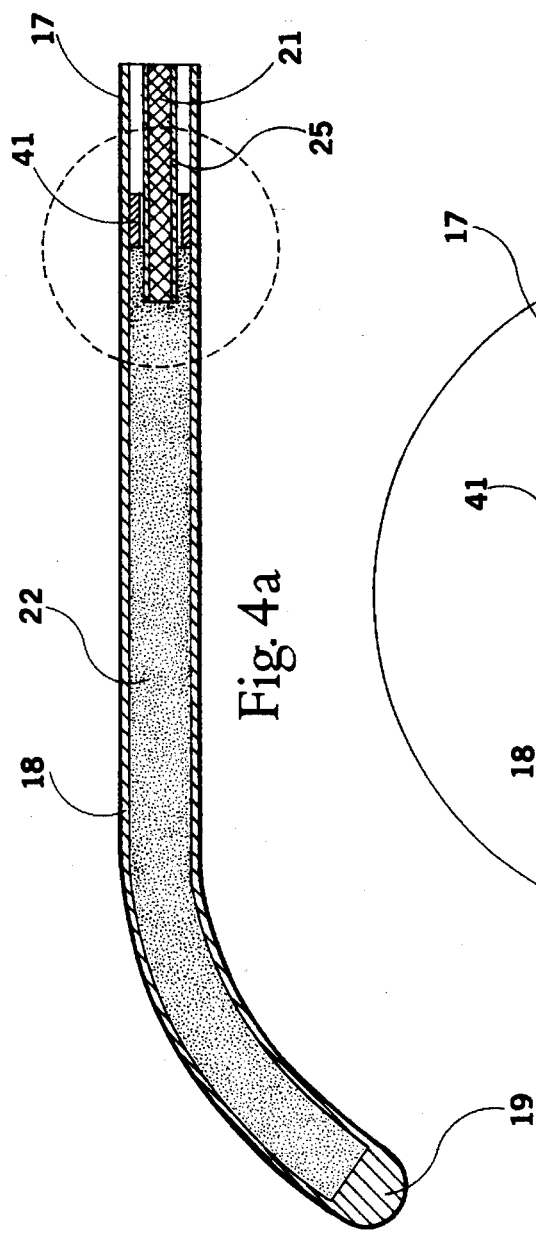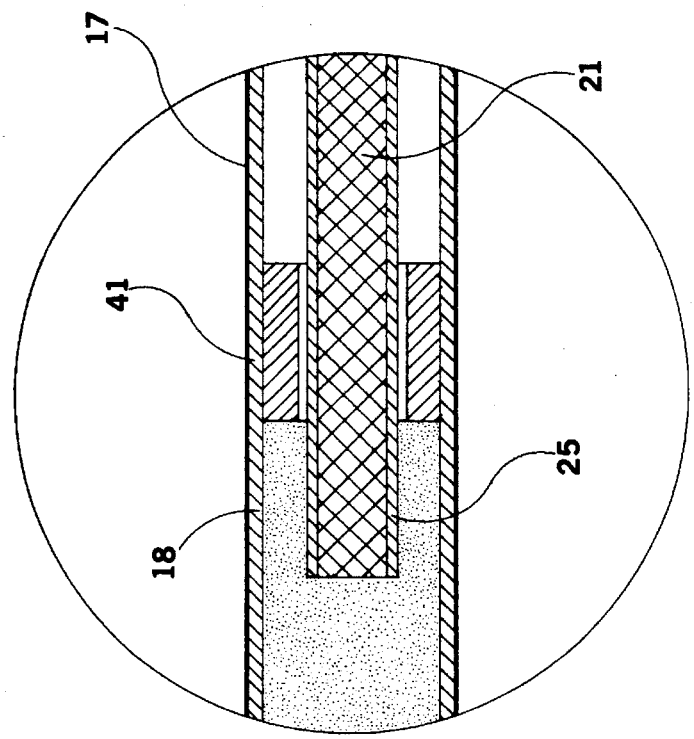

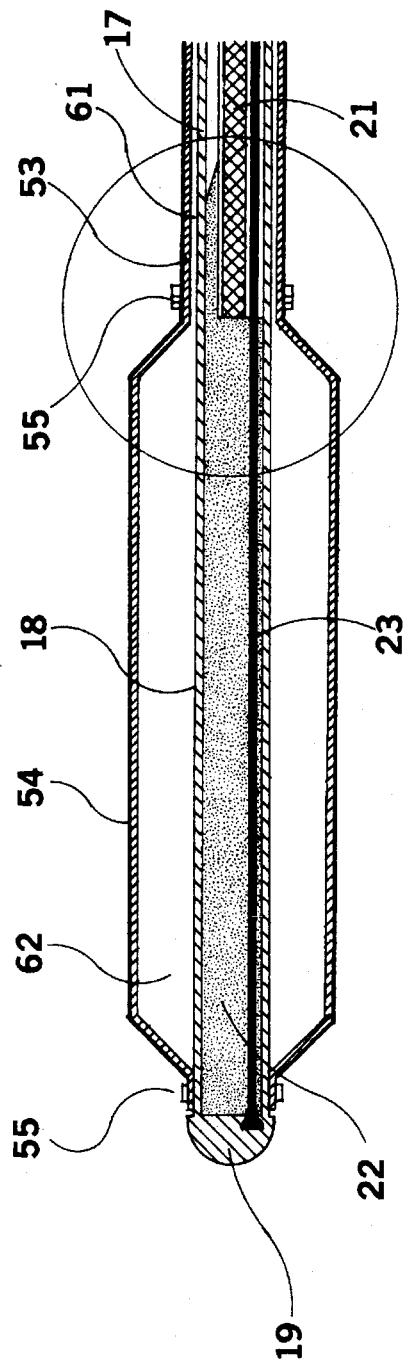
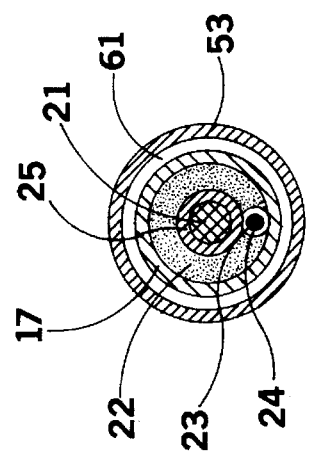
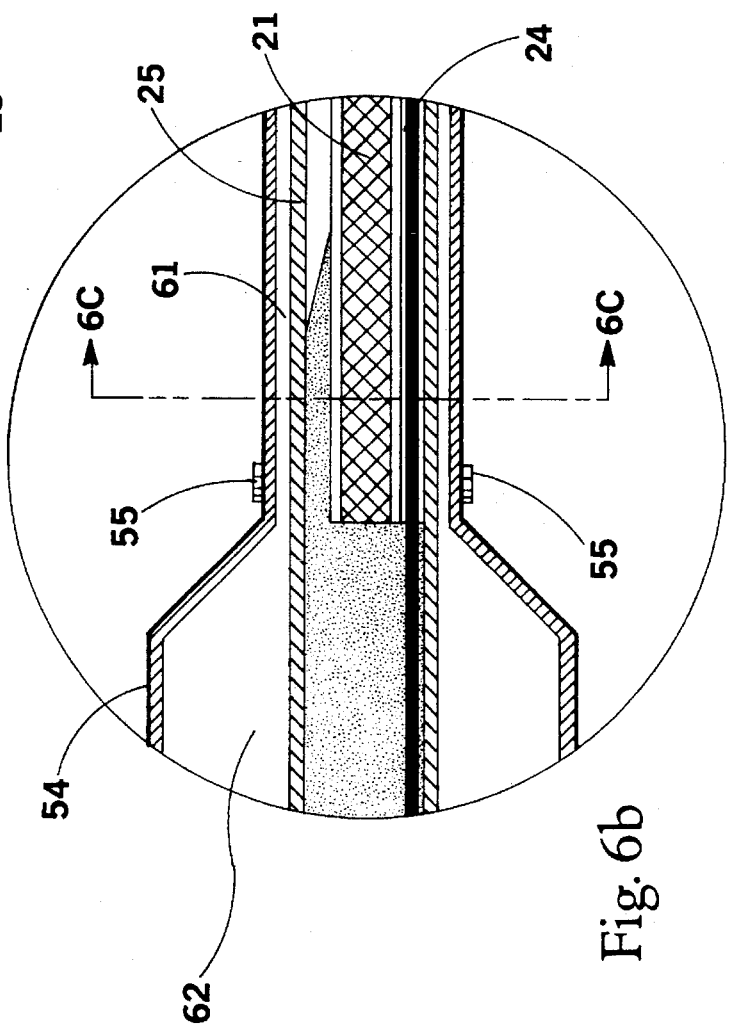
Fig. 6a
Fig. 6c
Fig. 6b

STEERABLE LIGHT DIFFUSING CATHETER

BACKGROUND OF INVENTION

1. Field of the Invention

This invention relates to a device for delivering light to a target situated beneath the skin of a patent for the diagnosis and/or treatment of a medical disease.

2. Reference to a Copending Patent Application

Reference is made to copending U.S. patent application Ser. No. 08/039,978 filed Mar. 30, 1993 and still pending, entitled "Transluminal Hyperthermia Catheter and Method for Use", having one inventor (Hugh L. Narciso, Jr.) in common with the present application.

3. Prior Art

Photodynamic Therapy (PDT) has been shown to be an effective method for treating tumors. PDT has also been proposed for the treatment of cardiovascular disease. Recently, the utility of PDT for the treatment of Benign Prostatic Hypertrophy (BPH) has been demonstrated. Delivery of light from a source (i.e. a laser) to the treatment site has been accomplished through the use of single fiber delivery systems with special light diffusing tips. As the field of PDT matures, new light delivery systems will be needed to treat specific sites. One such need is the ability to treat a small diameter lumen with a very flexible light diffusing catheter.

Delivery systems for PDT are well known in the art. Some examples include a single fiber cylindrical diffuser (Doiron, et al, U.S. Pat. No. 5,196,005), a spherical diffuser (McCaughan U.S. Pat. No. 4,693,556), a microlensing system (Narciso Jr., et al, U.S. Pat. No. 5,231,684), and an over-the-wire cylindrical diffusing multifiber optic catheter (Narciso Jr., U.S. Pat. 5,169,395), etc. While these systems have their uses in delivering diffuse light, they are generally not suitable for very small luminal applications.

A light diffusing catheter for use in the vascular tree is described by Narciso in U.S. Pat. No. 5,169,395. This device, which is designed to deliver therapeutic levels of light to a treatment site within the body is introduced into the body percutaneously and advanced to the target site via a guidewire. The guidewire acts as track to lead the catheter, permitting advancement only where the guidewire directs it. With a dedicated guidewire lumen, this catheter has a larger profile than is desirable for advancement into very small lumens. If an alternate guiding and steering method (to the guidewire method) can be employed, the overall catheter diameter can be substantially reduced thus allowing its use in small diameter tubular tissue such as blood vessels, small diameter lumen of the pulmonary tree, gastrointestinal tract, urological tract, and so forth.

SUMMARY OF THE INVENTION

It is the object of the present invention to provide a steerable light diffusing catheter with a tip that can be deflected during advancement of the catheter through the lumen of a tubular tissue.

It is a further object of the present invention to provide a light diffusing catheter wherein the tip can be deflected by extracorporeal means.

It is a further object of the present invention to provide a low profile light diffusing catheter which is can gain access to, and entry into, small diameter tubular tissue.

It is a further object of the present invention to provide a light diffusing catheter which is flexible.

It is a further object of the present invention to provide a light diffusing device which is easily constructed at low cost.

It is yet a further object of the present invention to provide a method in which said catheter may be used for both diagnostic and therapeutic applications.

The present invention solves the problems associated with the prior art light delivery catheters. Other objects as well as the scope and applicability of the present invention will become apparent to one skilled in the art from the following detailed description of the invention taken in conjunction with the accompanying drawings.

BRIEF DESCRIPTION OF DRAWINGS

FIG. 2a is a longitudinal cross-sectional view of the light diffusing tip of the SLID Catheter.

FIG. 2b is an enlarged view of the light diffusing tip of the SLID Catheter of FIG. 2a.

FIG. 2c is a cross-sectional view of the light diffusing tip of the SLID Catheter taken at 2c—2c.

FIG. 4a is a longitudinal cross-sectional view of the light diffusing tip of the SLID Catheter shown in FIG. 3.

FIG. 4b is an enlarged view of the circled portion of the light diffusing tip of the SLID Catheter of FIG. 4a.

FIG. 6a is a longitudinal cross-sectional view of the light diffusing tip of the SLID Catheter shown in FIG. 5.

FIG. 6b is an enlarged view of the circled portion of the light diffusing tip of the SLID Catheter of FIG. 6a.

FIG. 6c is a cross-sectional view of the light diffusing tip of the SLID Catheter taken at 6c—6c.

DESCRIPTION OF THE PREFERRED EMBODIMENT

The Steerable Light Diffusing (SLID) catheter of the present invention is useful for delivering light during a medical treatment such as Photodynamic Therapy, Photochemical Therapy, Photoablation Therapy, Photothermal Therapy, Light Induced Hyperthermia, Light Induced Photocoagulation, Tissue Welding, Light Surgery, Photodynamic Dosimetry, or Photo-Fluorescence Dosimetry. The SLID catheter of the present invention is also useful for fluorescence detection of abnormal cells and for diagnosis. The SLID catheter of the present invention overcomes the problems of steerability, flexibility, and large profile to reach small diameter lumen which cannot be accessed with prior art devices.

Figure 1:
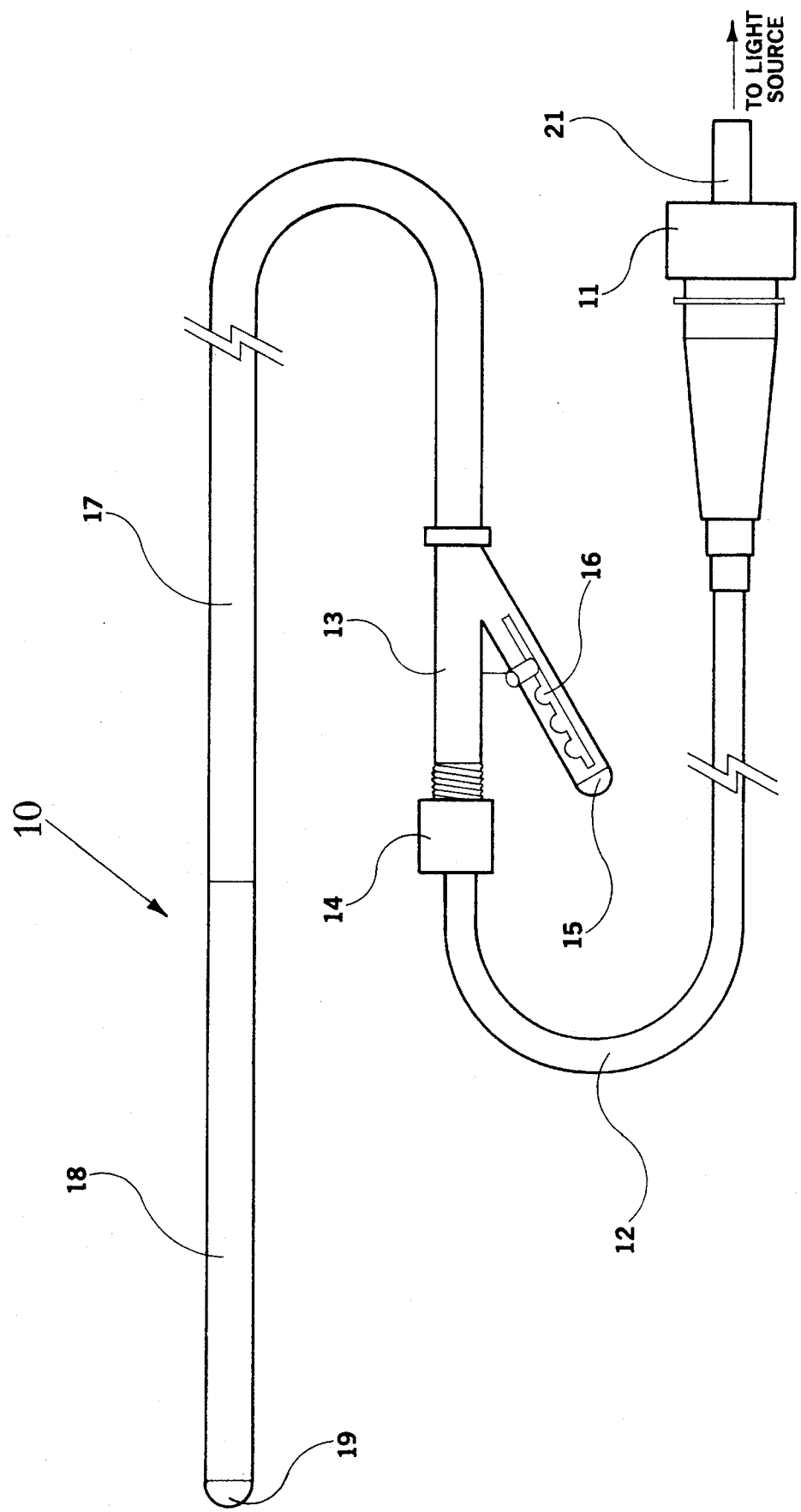
FIG. 1 is a schematic diagram of the Steerable Light Diffusing (SLID) Catheter of the present invention.

FIG. 1 shows a preferred embodiment of the Steerable Light Diffusing (SLID) catheter. The SLID catheter is generally indicated at the numeral 10. A fiber optic connector (11) is in optical communication with a light source (not shown). The light from the light source is delivered to a single fiber optic or bundle of optical fibers enclosed within the catheter sheath (12). The internal components of the distal catheter are separated at the Y-adapter (13) into the fiber optic port (14) and the tip deflection arm (15). Along the length of the tip deflection arm (15) is a spring loaded tip deflection controller (16). The tip deflection controller (16)

can be placed in any one of a series of slots which cause the tip to deflect a predetermined angle (i.e. 5, 15, 30, 45 degrees) or it may be infinitely adjustable and operable as a joystick. The deflecting tip wire, deflecting tip wire lumen, and the fiber optic (not shown in FIG. 1) are contained within the opaque catheter body (17) which is welded to an optically clear light diffuser tip (18) which tip (18) is terminated in a rounded cap (19). The materials used for the diffusing tip (18), the catheter body (17) and the catheter sheath (12) can be any suitable biocompatible plastic which has the optical and thermal properties required for this device to be operable such as Teflon®, polyester, polyurethane, polyethylene, polyethylene terephthalate, and so forth, or any sensible combination thereof.

FIGS. 2a and 2b illustrate longitudinal cross-sectional views of the distal end (20) of the SLID catheter (10) tip which includes from (FIG. 1) the rounded cap (19), and the diffuser tip (18). The fiber optic core and cladding (21) surrounded by a fiber optic buffer (25), delivers light energy from the light source (not shown) to the optical diffusing material (22). The optical diffusing material (22) is made from any optically clear flexible polymer (27) such as silicone or with optical scattering centers (28) such as alumina, titanium oxide, diamond dust, or calcium carbonate embedded therein. By varying the concentration of scattering centers (28) in the optically clear polymer (27) from lowest at the fiber optic (21)/diffusing material (22) interface to greatest at the rounded cap (19), either discretely or continuously, the light output distribution from the diffuser tip (18) can be made uniform both radially and axially. Embedded within the optical diffusing material (22) is a deflecting wire (23). The deflecting wire (23) is anchored within the rounded tip (19) distally and is introduced into the optical diffusing material (22) by means of the dedicated deflecting tip lumen (24). The deflecting wire (23) can be fabricated from any of a large number of metals which have the tensile strength and memory to deflect and return to its original position such as NITINOL, stainless steel, or tantalum.

FIG. 2c is a cross-sectional view of the light diffusing tip illustrating the relief (26) cut into the outer tubing of the tip (18) at 180 degrees of rotation from the deflecting wire (23) to facilitate the deflection of the tip (18).

Figure 3:
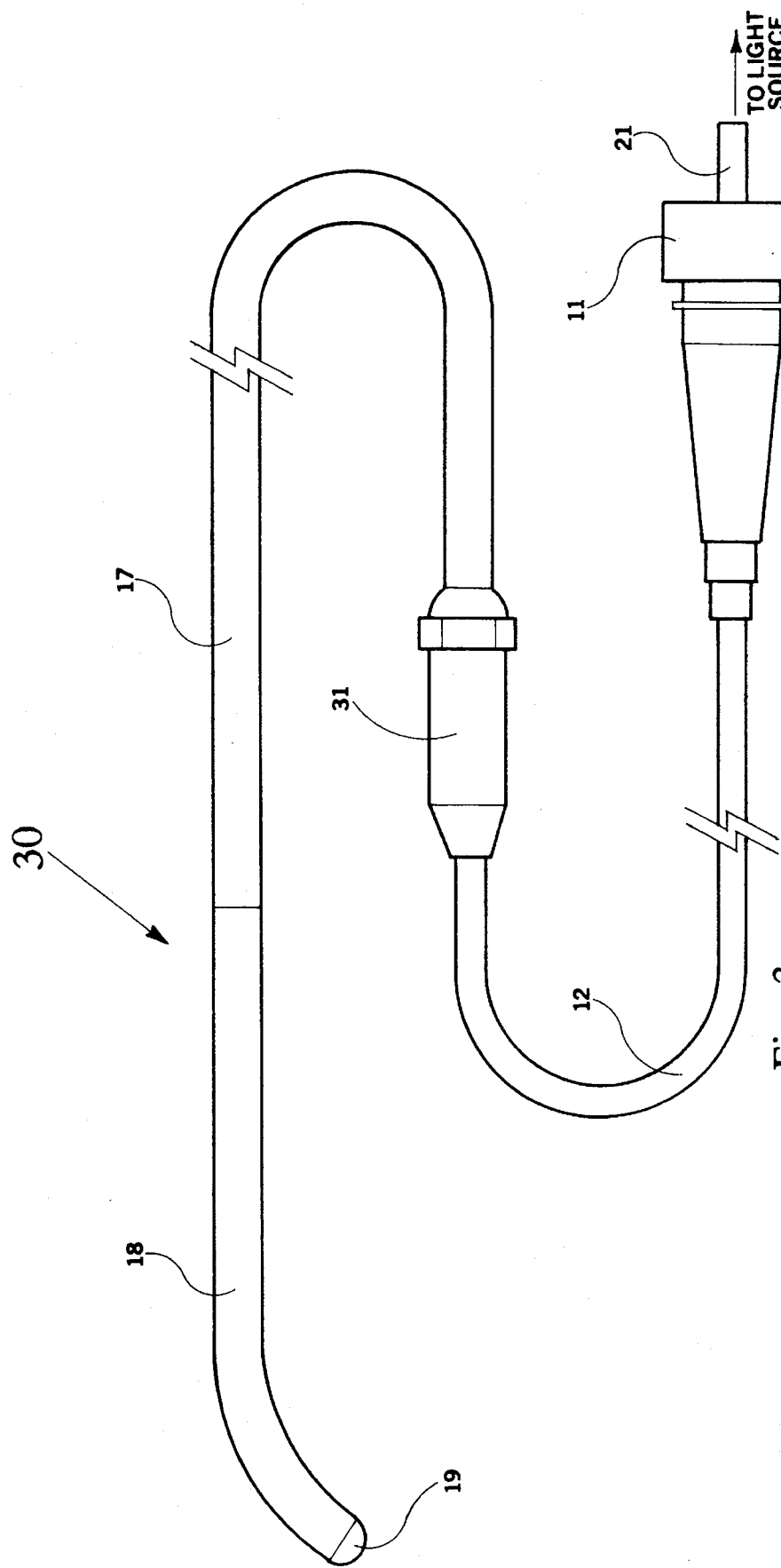
FIG. 3 is a schematic diagram of a second preferred embodiment of the SLID Catheter of the present invention.

FIG. 3 is a second preferred embodiment of the deflecting tip catheter generally shown at 30. The fiber optic connector (11) receives light energy from a light source, which light source is connected to the fiber optic tip by means of the fiber optic connector (11) (not shown) and transmits that light energy along the fiber optic contained within the catheter sheath (12). The fiber optic (21) is contained within the length of the catheter from the fiber optic connector (11) to the distal portion of the catheter body (17). The opaque catheter body (17) is welded to the optically clear diffuser tip (18) which terminates in the rounded cap (19). Between the catheter sheath (12) and the catheter body (17) is a torquing device (31) which is used to translate the rotation of the catheter to the rounded tip (19) from the portion of the catheter which is not introduced into the body.

FIGS. 4a and 4b are cross sectional views of the catheter tip shown in FIG. 3. The catheter body (17) is welded to the optically clear diffuser tip (18) which terminates in the rounded tip (19). The diffuser tip (18) is fabricated from a material which has memory to return the diffuser tip to a curved position in the most relaxed state. This is accomplished through the use of a plastic material with memory or the incorporation of a wire or spring within the wall of the diffuser tip (18) such as that used in catheter guidewires. Since wire is reflective and not transmissive to light, if wire is used, the catheter diffuser tip (18) must be extended to allow the deflecting portion of the catheter to extend beyond the light diffusing portion of the tip. The fiber optic (21) surrounded by a fiber optic buffer (25) is fixed concentrically in the lumen created by the catheter body (17) by a spacer (41).

Figure 5:
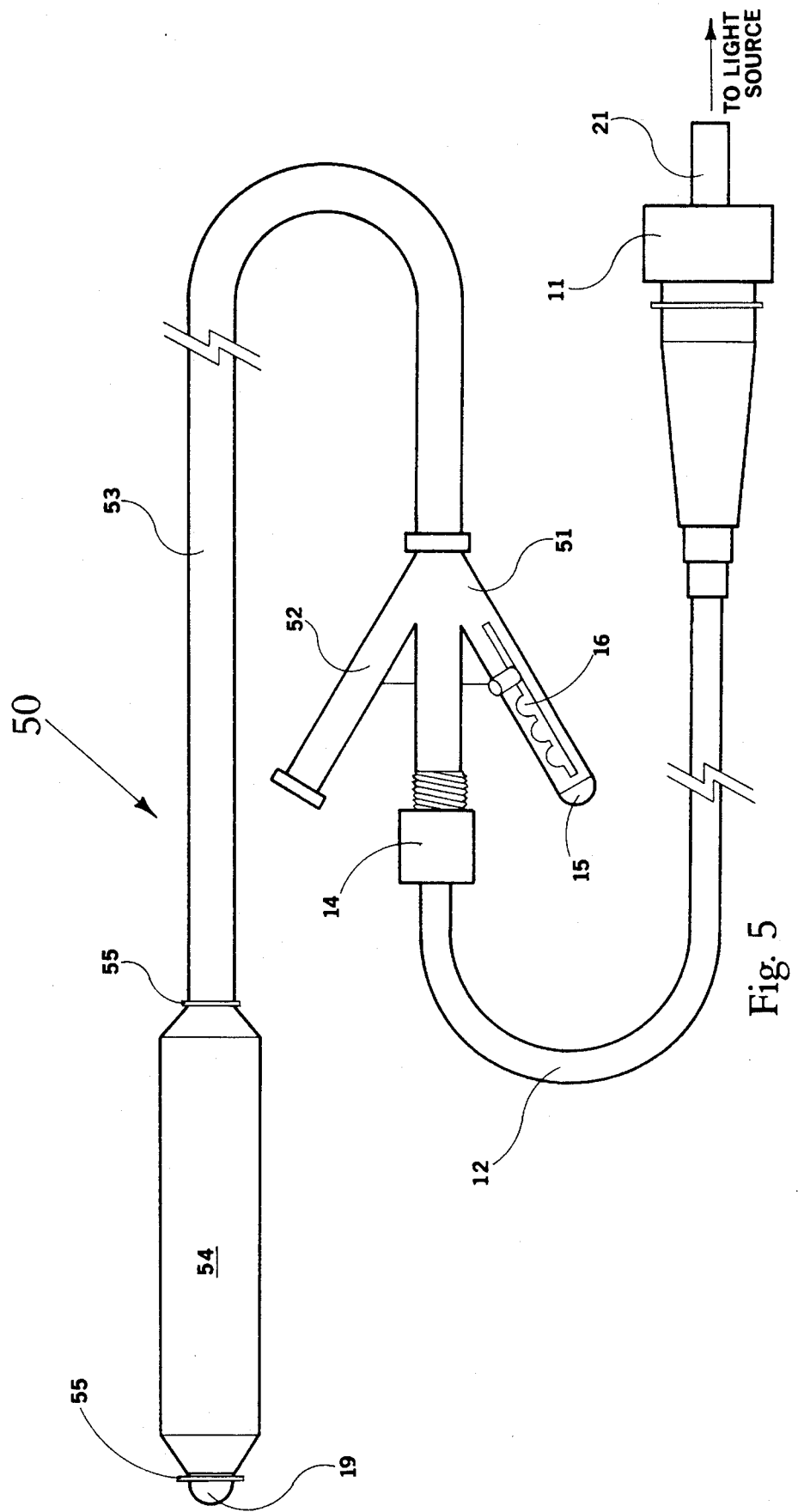
FIG. 5 is a schematic diagram of a third preferred embodiment of the SLID Catheter of the present invention.

FIG. 5 is a third preferred embodiment of the SLID catheter generally indicated at 50. The fiber optic (21), catheter sheath (12), fiber optic port (14), tip deflection arm (15), and the tip deflection controller (16) have the same function and arrangement as described in FIG. 1. The Y-adapter (13) is replaced with a three arm adapter (51) which incorporates a balloon inflation/deflation port (52). The balloon inflation/deflation port (52) allows the addition of a fluid through an inflation/deflation channel (not shown in this figure) created within the external sheath (53) to the balloon (54) which terminates in the rounded cap (19). Distal and proximal to the balloon are marker bands (55) for visualization under X-ray fluoroscopy.

FIGS. 6a, 6b and 6c are cross sectional views of the catheter tip shown in FIG. 5. The fiber optic core and cladding (21) is surrounded by a fiber optic buffer which in turn is surrounded by the optical scattering mixture (22) which in turn is surrounded by the catheter body (17) which in turn is surrounded by the inflation/deflation channel (62) which in turn is surrounded by the external sheath (53). Between the catheter body (17) and the fiber optic buffer is the dedicated deflecting tip lumen (24) which surrounds the deflecting wire (23).

The internal construction is identical to that shown in FIG. 2 with the addition of the external sheath (53) which creates the inflation/deflation channel (61). The inflation/deflation channel delivers the inflation fluid (62) to the balloon (54) and thus inflates the balloon (62). On each side of the balloon (62) is placed a marker band (55) for visualization under X-ray fluoroscopy.

The diameter of the catheter without the balloon can be made as small as 0.028"based on an optical fiber with a 200 micron core or smaller if a smaller core optical fiber (i.e. 50–100 microns in diameter) is employed. With the addition of the balloon, the catheter can be used to treat lesions in vessel with a diameter less than one millimeter.

The above is a detailed description of three particular embodiments of the invention. It is recognized that departures from the disclosed embodiments may be within the scope of this invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What we claim is:

1. An intraluminal catheter for delivering light energy from a source of optical energy to a tissue undergoing optical energy treatment, or receiving an optical signal from tissue, said light energy being delivered in a uniform cylindrical pattern, said catheter comprising:

(a) A tubular body portion having a first proximal end and a first distal end;

(b) An optically transmissive member coextensive with at least a portion of said body portion, said optically transmissive member terminating at said first distal end of said body portion;

(c) A flexible cylindrical light diffusing tip having a second proximal end attached to a said first distal end of said body portion in optical communication with said optically transmissive member, and a second distal end having a cap attached thereto;

(d) Means for coupling said light energy from said source of optical energy into said optically transmissive member;

(e) A tip deflection means extended from said end and terminating in a controlling device, wherein said controlling device is positioned between said light diffusing tip and said means for coupling light energy from said source of optical energy into said optically transmissive member.

(f) An optically transparent inflatable balloon enveloping at least a portion of said light diffusing tip.

(g) Means for inflating said inflatable balloon.

2. The catheter of claim 1 where the said optically transmissive member is a single optical fiber.

3. The catheter of claim 1 where the said optically transmissive member is a plurality of fiber optics.

* * * * *